United States Patent [19]

Parren

[11] Patent Number: 4,781,698

[45] Date of Patent: Nov. 1, 1988

[54] SELECTABLE DROP SIZE INFUSION METERING DEVICE

[76] Inventor: Mark L. Parren, 712 Broad St., St. Joseph, Mich. 49085

[21] Appl. No.: 34,540

[22] Filed: Apr. 9, 1987

[51] Int. Cl.$^4$ .............................................. A61M 5/14
[52] U.S. Cl. .................................. 604/246; 604/248; 604/251; 604/81
[58] Field of Search ................ 604/246, 81, 248–252, 604/127, 253–255; 251/125, 206; 138/45–46; 272/420–422

[56] References Cited

U.S. PATENT DOCUMENTS

| | | | |
|---|---|---|---|
| 2,247,227 | 6/1941 | Findley | 251/86 |
| 2,576,403 | 11/1951 | Kirschenbaum | 222/421 |
| 2,812,765 | 11/1957 | Tofflemire | 128/276 |
| 3,298,367 | 1/1967 | Bergman | 128/214 |
| 3,323,774 | 6/1967 | Wilson | 251/125 |
| 3,341,168 | 9/1967 | Toeppen | 251/148 |
| 3,517,909 | 6/1970 | Santomieri | 251/342 |
| 3,690,318 | 9/1972 | Gorsuch | 604/246 X |
| 3,785,378 | 1/1974 | Stewart | 128/214 |
| 3,877,428 | 4/1975 | Seagle et al. | 128/214 |
| 3,878,869 | 4/1975 | Yamanouchi et al. | 138/40 |
| 3,880,401 | 4/1975 | Wiltse | 251/205 |
| 3,949,966 | 4/1976 | Fabish | 251/206 |
| 4,195,631 | 4/1980 | Baucom | 251/206 |
| 4,317,473 | 3/1982 | Gaydos | 251/206 X |
| 4,468,225 | 8/1984 | Tcheraz | 604/248 |
| 4,553,964 | 11/1985 | Sasaki | 604/248 |
| 4,694,856 | 9/1987 | Leibinsohn | 604/251 X |

FOREIGN PATENT DOCUMENTS 2635855  2/1979  Fed. Rep. of Germany .
1347759 11/1963  France .

Primary Examiner—Dalton L. Truluck
Attorney, Agent, or Firm—Price, Heneveld, Cooper, DeWitt & Litton

[57] ABSTRACT

An infusion system capable of intravenous administration of fluid to a patient has a drop chamber, including a plurality of drop tubes having drop forming orifices of different preselected cross-sectional areas for forming droplets of different sizes and volumes of the same given fluid, selection means for selecting the drop tube through which the administered fluid will pass and a metering chamber to allow the rate of droplet flow to be observed. The drop tube having a drop orifice capable of producing droplets of the desired size and volume appropriate for the viscosity and purpose of the fluid being administered is selected and a conventional fluid flow rate control device is adjusted, while the drop rate is observed, to set the fluid flow rate. The present invention allows a change of the fluid being administered, without disassembling the apparatus or removing it from the patient by replacing the fluid resevoir, or by valving a different fluid reservoir to the drop chamber and by operating the selection means in order to select the drop tube capable of forming the size and volume droplet appropriate for the viscosity and purpose of the substituted fluid. The flow rate control device may then be adjusted to set the flow rate for the substituted fluid.

15 Claims, 2 Drawing Sheets

SELECTABLE DROP SIZE INFUSION METERING DEVICE

BACKGROUND OF THE INVENTION

The present invention relates to intravenous fluid infusion apparatus and, in particular, to such infusion apparatus capable of administering variable volumes of the same or a different fluid to a patient.

Conventional apparatus for intravenous infusion of fluids utilizes an elevated fluid receptacle connected by flexible conduit or tubing to the hub of a catheter or needle inserted into the patient. A flow control device regulates the rate of fluid flow through the tubing and a metering device, called a drop chamber, provides a means to measure the fluid flow rate. A conventional drop chamber comprises a drop tube having a single drop forming orifice that separates the fluid stream into a series of individual droplets that then fall by gravity through a hollow transparent body to allow the droplets to be monitored. By knowing the volume of each droplet, which is determined by the size of the drop orifice and is labeled on the packaging of the apparatus, the rate of fluid administration can be determined by counting the rate of droplet formation or drop rate. The flow control device is adjusted while the drop rate is monitored to control the fluid administration rate.

The viscosities of different parenteral fluids vary greatly. For example, aqueous base solutions have a low viscosity while whole blood and blood plasma have relatively high viscosities. As a result, it is necessary to select a drop chamber having a drop tube orifice that corresponds to the droplet volume appropriate for the fluid used. A 60 drop per cubic centimeter orifice, suitable for administering saline solution, would clog if attempted to be used for administering blood. At other times, a very small orifice is required to administer very small amounts of fluid because of the concentration of the medicine in the solution and the necessity of accurate infusion.

Because of the foregoing limitation, it is necessary to change to a different drop chamber, having an appropriate drop orifice size, whenever it is necessary to administer a fluid having a viscosity significantly different from the one currently being administered. This change in apparatus, which is sterile, increases the risk of contaminating the patient. In addition, valuable time is spent in selecting the appropriate drop chamber, in reconnecting the apparatus and in evacuating air from the apparatus. Further, if the wrong drop tube is selected in an emergency situation, the apparatus must be disconnected and the proper apparatus connected. Changing of the apparatus, as with any medical procedure, may be stressful to a patient and is therefore best kept to a minimum. Finally, increased expenses are associated not only with the use of multiple apparatus sets for each patient but also with the necessity to inventory several different orifice size drop chambers.

Many medical procedures require a change in the fluid being intravenously administered to the patient. For example, a trauma patient is stabilized in an ambulance using an aqueous base solution. Once the trauma patient arrives at the treatment facility, and their blood type can be determined, whole blood or blood plasma may then be administered, if indicated. As another example, major surgery such as coronary artery by-pass, requires that whole blood or blood plasma be administered to the patient during the actual procedure and aqueous base solution administered after the patient is sutured. Should hemorrhaging develop and additional surgery be required, the patient must be taken off of the glucose or saline solution and again be administered whole blood or blood plasma.

SUMMARY OF THE INVENTION

Accordingly, it is an object of the invention to overcome the above difficulties by providing an intravenous fluid infusion device that is capable of delivering multiple fluids, having greatly different viscosities, or minute or large volumes of the same or different fluids to a patient in sequence, or seriatim, without requiring a change in apparatus, thus minimizing life-threatening delays during an emergency as well as routine medical procedures. It is a further object of the present invention to provide such an infusion device that corresponds to the conventional droplet monitoring technique and will, therefore, be acceptable to medical practitioners. According to the invention, an infusion system for intravenous administration of fluids to a patient from a fluid reservoir, has a drop chamber including a drop orifice capable of splitting the stream of fluid flow into a sequence of droplets and a metering chamber to allow the rate of droplet flow to be monitored. The orifice can be selectively varied in cross-sectional area by operation of a selection means to create droplets of a size appropriate for the viscosity of the administered fluid or to infuse greatly varying volumes of the same fluid. The invention is to be used in conjunction with a flow control device of the type that is well-known in the art.

In a preferred embodiment, the orifice and metering chamber are combined in a unitary device and comprise upper and lower cylindrical members rotatable with respect to each other. The lower chamber has a plurality of drop tubes, each having a different preselected diameter drop orifice, circumferentially spaced around a mounting plate. The upper chamber has a lower disk abutting the orifice mounting plate and a discharge opening formed in the disk that is selectively alignable with one of the plurality of drop tubes. The diameter of the particular drop tube orifice that is aligned with the discharge opening determines the size of the droplet that will be formed. The lower chamber has a pliable transparent wall in order to allow the drop rate to be monitored.

These and other related objects, advantages and features of this invention will become apparent upon review of the following specification in conjunction with the drawings.

DESCRIPTION OF THE PREFERRED EMBODIMENT

Figure 1:
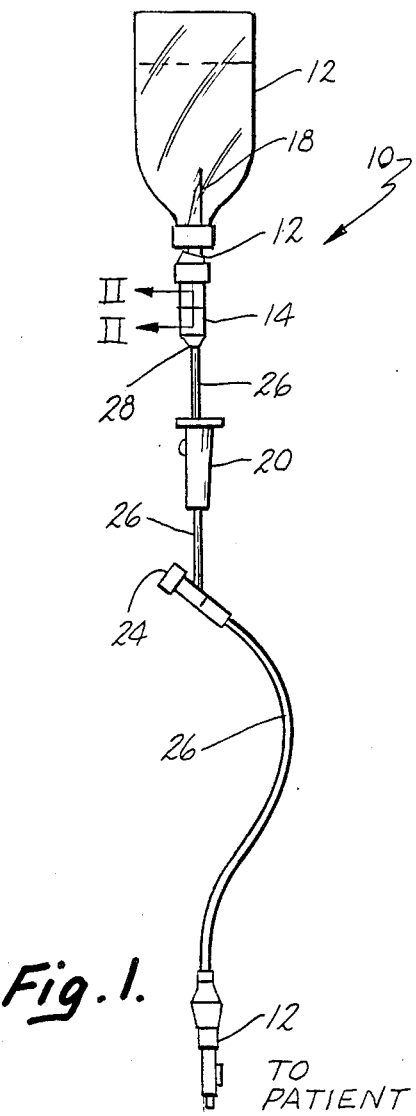
FIG. 1 shows a multi-fluid infusion device according to the present invention.

Referring now specifically to the drawings, and the illustrative embodiments depicted therein, a multi-fluid infusion system 10 has a fluid reservoir 12, preferably of the collapsible bag type, that is supported above a patient by a rack member (not shown). A metering device or drop chamber 14 is connected to reservoir 12 by a supply tube 18 that punctures and extends into reservoir 12. A flow control device 20, illustratively shown as a roller clamp, is connected to drop chamber 14 by tubing or conduit 26 and is connected to a feed tube 22 that is configured for insertion into the hub of a catheter or needle inserted into the patient. A supplemental administration port 24 in the tubing 26 that connects the flow control device 20 to feed tube 22, is utilized to administer small dosages of medication into the infusion system by the insertion of a hypodermic needle into port 24. Substantially, all of the above components are made of elastomeric material. The components are packaged in a sterilized kit and are disposable after use.

Figure 5:
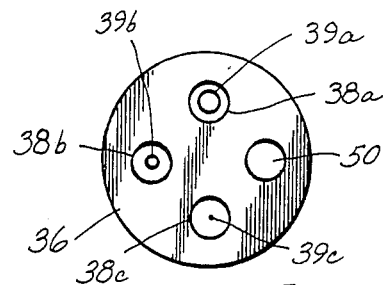
FIG. 5 is an end view taken along the lines V—V in FIG. 3.
Figure 2:
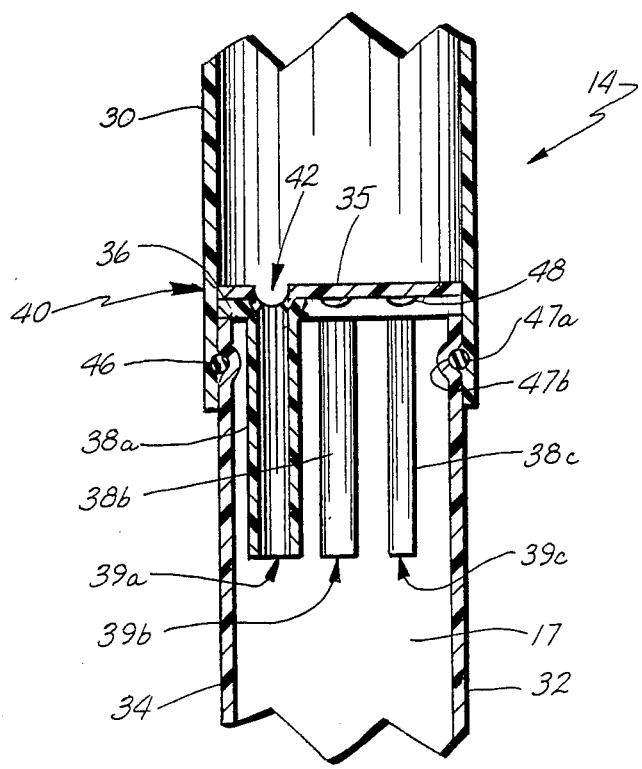
FIG. 2 is a sectional side elevation view taken along the lines II—II in FIG. 1.

Metering device or drop chamber 14 is shown in detail in FIG. 2. Drop chamber 14 is comprised of a first, upper member 30 and a second, lower member 32 that are both cylindrical in shape. Lower member 32 is partially telescopically received within upper member 30 and is rotatable with respect to upper member 30 forming a selection means generally shown at 40. The top portion of lower member 32 is sealed by a mounting plate 36 and the bottom portion thereof defines a fluid outlet 28. A plurality of drop tubes 38a, 38b and 38c penetrate through, and are circumferentially spaced around, mounting plate 36, as best seen in FIG. 5. Drip tubes 38a-c have lower edge means defining drop forming orifices 39a-c, respectively. Each orifice 39a-c has a different cross-sectional area. The orifice cross-sectional areas are preselected to produce droplets of various volumes appropriate for the viscosity of the fluids that will be administered with the apparatus, or to infuse greatly varying volumes of the same fluid.

A fluid inlet 27 forms the top of upper member 30. A disk 35 forms the bottom of upper member 30 and is in general abutting relationship with mounting plate 36. A discharge opening 42 formed in disk 35 is offset from the central longitudinal axis of members 30, 32 a preselected distance so as to be selectively alignable with one of the drop tubes 38a, 38b or 38c. A flexible edge or wiper means 44 formed around opening 42 provides a seal between disk 35 and the selected drop tube to prevent any of the administered fluid from seeping in between disk 35 and mounting plate 36.

Figure 3:
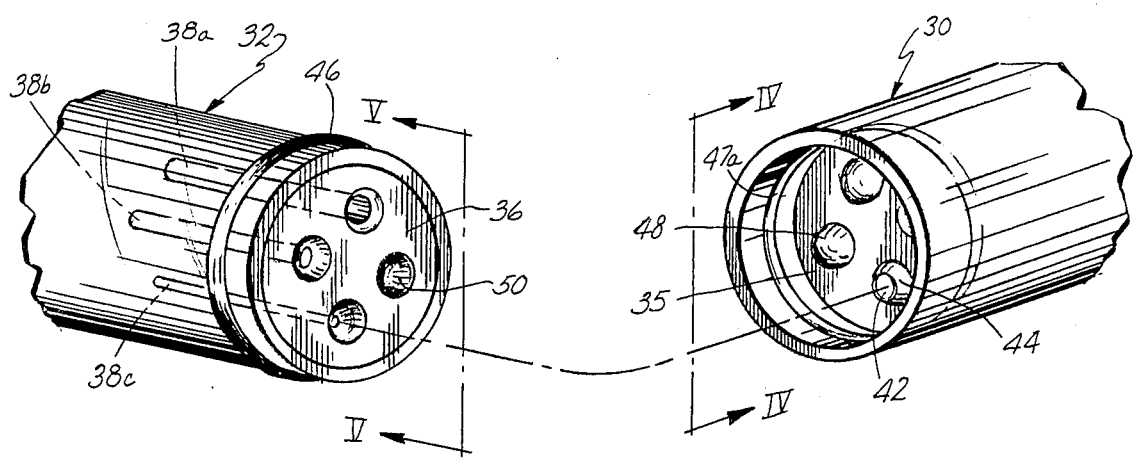
FIG. 3 is an exploded perspective view of the device shown in FIG. 2.

As best seen in FIG. 3, a plurality of downwardly extending debosments 48 are radially spaced around disk 35 in the same general configuration that the drop tubes 38a-c are spaced around mounting plate 36. The upper portion of drop tubes 38a, 38b and 38c that protrude through mounting plate 36 are enlarged to approximately the same size as debosments 48. Thus, when selection means 40 is operated to selectively align discharge opening 42 with one of the drop tubes 38a-c, debosments 48 will rest in the enlarged portion of the nonselected drop tubes to retain the members 30, 32 in their selected orientation. A detent 50 in mounting plate 36 does not penetrate through mounting plate 36 and serves as an off position that discharge opening 42 can be aligned with when no flow is desired. An O-ring seal 46 seated in grooves 47a, 47b on members 30, 32 prevents contamination of the interior of drop chamber 14 and serves as coupling means for retaining members 30, 32 together. A metering chamber 17 below orifices 39a-c has a pliable cylindrical wall 34 that is transparent, to facilitate monitoring of liquid droplets dispensing from the selected orifice as will be described in more detail below.

The above described apparatus operates as follows. When it is desired to infuse a particular liquid into a patient, a needle or catheter is inserted in the patient and the apparatus is connected in the manner previously described. As is conventional, air must be first evacuated from the apparatus before the apparatus is connected to the patient by flowing fluid through the apparatus until all of the air is expelled. This can advantageously be performed very rapidly with the present invention by setting control device 20 to maximum flow and selectively aligning the discharge opening 42 with drop tube 38a having the largest orifice 39a. This aligning is accomplished by operating selection means 40, i.e., by rotating first member 30 with respect to second member 32, until discharge opening 42 is in alignment with drop tube 38a.

Once the apparatus is purged of air, flow control device 20 is closed and selection means 40 is operated in order to align discharge opening 42 with the drop tube 38a-38c that is appropriate for the fluid to be administered. Once the appropriate selection is effected, flow control device 20 is regulated, while the rate of droplet flow from the selected drop tube orifice through metering chamber 17 is monitored, to establish the desired flow rate. If it is desirable to administer a fluid having a significantly different viscosity to the patient, flow control device 20 is closed off and the fluid reservoir 12 is exchanged for another one having the desired fluid therein. Selection means 40 is operated in order to align discharge opening 42 with the drop tube 38a-c having the drop orifice 39 that is appropriate for the viscosity of the fluid that is to be administered and flow control device 20 is regulated while the drop rate is monitored in metering chamber 17.

Members 30, 32 would be inscribed with appropriate indicia (not shown) to clearly indicate the droplet volume of the selected orifice 38 and the indicia may be appropriately color coded with the various fluid reservoirs. In the illustrated embodiment, orifices 39a-c would have diameters corresponding to 10 drops per cubic centimeter (cc), 15 drops per cc and 60 drops per cc, respectively. Any appropriate drop size orifices could be utilized and the number of drop tubes could be fewer than or more than that shown.

The decrease in the time required to purge the apparatus of air can be significant. For example, if saline or like solution requiring the smallest orifice is to be administered, the air purging time for conventional infusion apparatus would be approximately 30 seconds. By using the largest orifice in the present invention, the lines can be purged in about 5 seconds and the selection means then operated in order to administer the low viscosity fluid. Advantageously, a momentary increase in the rate of flow of the infused fluid can also be of help in forcing medication applied in supplemental administration port 24 to the patient rapidly when desired.

Figure 6:
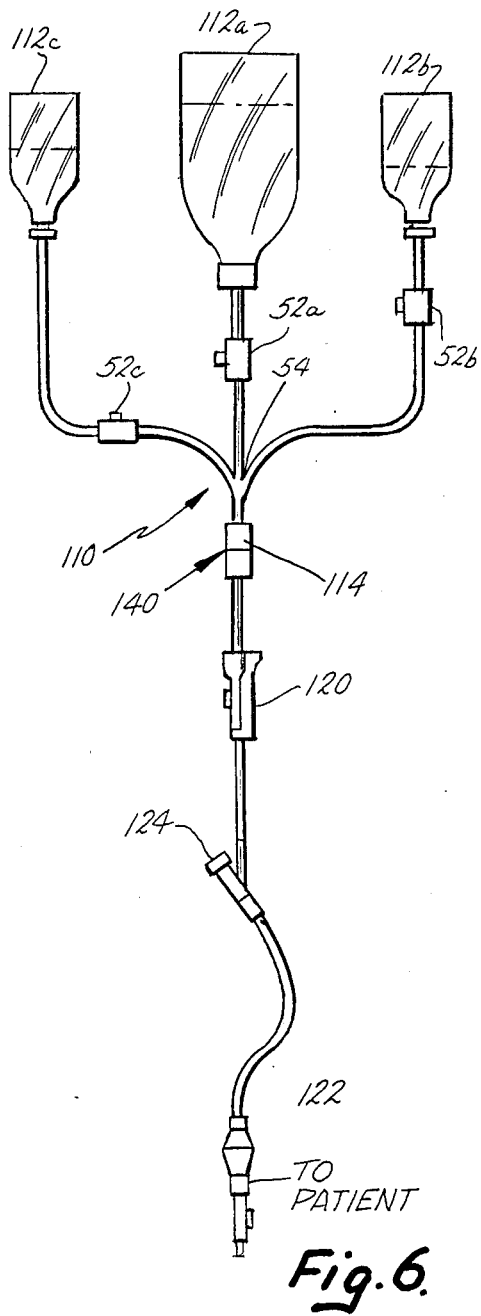
FIG. 6 shows a multi-fluid infusion device connected to multiple fluid reservoirs.
Figure 4:
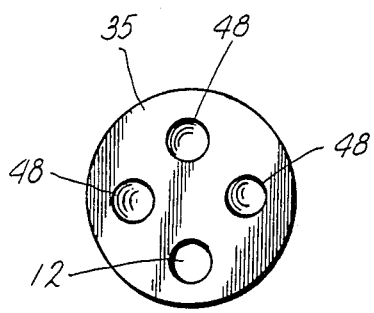
FIG. 4 is an end view taken along the lines IV—IV in FIG. 3.

FIG. 6 shows an arrangement of components according to the present invention when it is contemplated ahead of time that multiple fluids will need to be administered to a patient. Such a situation would typically arise during major surgical treatment in which the patient is stabilized on glucose or saline solution before surgery, is administered whole blood or blood plasma during surgery and may be administered yet another fluid after surgery. A plurality of fluid reservoirs 112a–c are each connected to a common connection 54 through a shut off roller clamp or valve 52a–c. Connection 54, in turn, is connected to drop chamber 114. In the following example, it will be assumed that fluid reservoir 112a contains saline solution, reservoir 112b contains whole blood, and reservoir 112c contains glucose.

To purge the apparatus before connecting to the patient, clamps 52a, 52b and 52c are initially closed. Clamp 52b will be momentarily opened to purge the short section of tubing from the blood reservoir 112b to common connection 54. Clamp 52b is then closed and clamp 52c momentarily opened in order to purge the tubing from reservoir 112c to the connection 54. Purging is completed by closing valve 52c and opening valve 52a to purge the remainder of the apparatus with the saline solution in reservoir 112a. Assuming that saline solution is the first fluid to be administered, valve 52a is momentarily closed while selection means 140 is adjusted to select the drop tube appropriate for saline solution. Valve 52a is then opened and flow control device 120 adjusted to the desired flow rate by monitoring the drop rate. When it then becomes desirable to administer whole blood, clamp 52a is closed and selection means 140 adjusted to select the drop tube appropriate for blood. Clamp 52b is then opened and flow control device 120 adjusted for the appropriate flow. To subsequently administer glucose solution, clamp 52b is closed and selection means 140 adjusted to select the appropriate drop tube. Clamp 52c is then opened and flow control device 120 adjusted.

It is thus seen that the present invention provides multi-liquid infusion capability that greatly reduces the time required to intravenously administer fluids by not only eliminating the requirement to change apparatus every time a different fluid is administered, but also by reducing the amount of time required to establish the apparatus. The largest orifice may be used to purge the line of air with subsequent selection of the proper drop setting for infusion. Furthermore, wasting precious time that may be lost by the selection of a drop tube that is inappropriate for the desired fluid can be completely eliminated. The present apparatus would reduce the cost of administering multiple fluids by requiring that only one apparatus be used on the patient no matter how many different fluids are administered. Inventory costs are also reduced because only one type of apparatus, rather than three or four, need to be maintained in inventory. Finally, most importantly, the patient's well-being is enhanced by the reduced risk of infection and the stress associated with the procedure of fluid infusion apparatus changeover.

Changes and modifications in the specifically described embodiments can be carried out without departing from the scope of the invention which is intended to be limited only by the scope of the appended claims.

The embodiments of the invention in which an exclusive property or privilege is claimed are defined as follows:

1. An infusion system for intravenous administration of fluid to patient from a fluid reservoir comprising:
   a drop chamber;
   first connecting means for connecting said drop chamber to a fluid reservoir;
   adjustable drop forming means in said drop chamber for splitting a stream of a fluid into sequentially discharged droplets;
   metering means connected to said drop chamber for metering the rate the droplets are discharged from said drop forming means;
   second connecting means for connecting said metering means to a patient;
   flow control means located in one of said connecting means for varying the flow rate of fluid to a patient; and
   selection means associated with said drop chamber for selectively adjusting said drop forming means to selectively produce droplets of different size and fluid volume for a given fluid, said selection means operable to adjust said drop forming means without disconnecting any portion of said system;
   whereby the selection means may be operated to produce droplets of a size and volume appropriate for the viscosity of the fluid being administered and the desired rate of fluid infusion without disassembling the system or disconnecting the system from a patient.

2. An infusion system for intravenous administration of fluid to a patient from a fluid reservoir comprising:
   a drop chamber;
   first connecting means for connecting said drop chamber to a fluid reservoir;
   adjustable drop forming means in said drop chamber for splitting a stream of a fluid into sequentially discharged droplets;
   metering means connected to said drop chamber for metering the rate the droplets are discharged from said drop forming means;
   second connecting means for connecting said metering means to a patient;
   flow control means located in said second connecting means for varying the flow rate of fluid to a patient; and
   selection means associated with said drop chamber for selectively adjusting said drop forming means to selectively produce droplets of different size and fluid volume for a given fluid, said selection means operable to adjust said drop forming means without disconnecting said first connecting means from said drop chamber;
   whereby the selection means may be operated to produce droplets of a size and volume appropriate for the viscosity of the fluid being administered and the desired rate of fluid infusion without disassembling the system or disconnecting the system from a patient; and said drop forming means comprising a plurality of drop tubes, each of said drop tubes having an orifice of a cross-sectional area different from that of the other said drop tubes and said selection means comprises flow directing means for directing fluid to one of said drop tubes.

3. The infusion system in claim 2 wherein said drop tubes are circumferentially spaced in a circle having a predetermined diameter and said flow directing means comprises a disk selectively rotatable concentrically with said circle of tubes and having edge means for defining a discharge opening selectively alignable with one of said tubes.

4. The infusion system in claim 3 wherein said tubes are equally circumferentially spaced and wherein said disk further has surface means defining a debosment circumferentially spaced from said discharge opening and extending toward said tubes for retaining said discharge opening aligned with said one of said tubes.

5. The infusion system of claim 4 wherein said surface means defines a plurality of such debosments.

6. The infusion system of claim 3 wherein said edge means further defines a flexible wiper means for sealing said discharge opening with said one of said orifices.

7. A metering device for an intravenous fluid infusion system having a fluid resevoir, conduit means for connecting said reservoir to a patient and a flow control means for controlling the rate of fluid flow through said conduit means, said metering device comprising:

a first member having a fluid inlet and a discharge opening;

a second member having a mounting plate, a plurality of drop tubes mounted to said mounting plate and a fluid outlet;

sealing means between said members for preventing contamination from entering said metering device;

each one of said drop tubes having an orifice of cross-sectional area capable of splitting a stream of fluid into sequentially discharged droplets having a predetermined droplet size and volume for a given fluid viscosity, the cross-sectional area of each drop tube different from the cross-sectional area of the other said drop tubes;

selection means for selectively aligning said discharge opening with one of said drop tubes; and metering means between said drop tubes and said fluid outlet for metering the rate of droplet production by said one of said drop tubes.

8. The metering device of claim 7 wherein said second member has a wall means for enclosing said drop tubes and wherein said metering means comprises said wall means being substantially transparent.

9. The metering device of claim 7 wherein said alignment means comprises said drop tubes being circumferentially spaced on said mounting plate in a circle of predetermined diameter, coupling means for coupling said first member to said second member for rotation therewith coaxially with said circle and said discharge opening being located in alignment with said circle.

10. The metering device of claim 7 wherein said plurality of drop tubes comprises three drop tubes capable of producing droplets having volumes of 10 drops per cc, 15 drops per cc and 60 drops per cc, respectively.

11. A metering device for an intravenous fluid infusion system having a fluid reservoir, conduit means for connecting said reservoir to a patient and a flow control means for controlling the rate of fluid flow through said conduit means, said metering device comprising:

a drop chamber having first and second members having cylindrical walls generally vertically aligned along a central longitudinal axis and rotatable with respect to each other about said axis defining a selection means for selectively orienting said members;

said first member having a fluid inlet and a bottom disk attached to said cylindrical wall, said bottom disk having edge means defining a discharge opening spaced a predetermined distance from said axis;

said second member having a top mounting plate abutting said disk, a plurality of drop tubes mounted to said plate and a fluid outlet, said plate attached to the other said cylindrical wall;

each said drop tube having an edge means defining a drop orifice, each said drop orifice of different cross-sectional areas than the other said drop orifices; and said drop tubes parallel with said axis and circumferentially spaced in a circle around said axis, said circle having a radius equal to said predetermined distance;

whereby the first member discharge opening is selectively alignable with one of said drop tubes by rotating said first chamber with respect to said second chamber to select a drop orifice capable of producing droplets of a volume appropriate for the viscosity of the fluid being administered and the desired rate of fluid infusion.

12. The metering device in claim 11 wherein said second member cylindrical wall is transparent to provide means for determining the rate of droplet formation.

13. The metering device in claim 11 having means defining aligned grooves on said first and second member cylindrical walls and a seal in said groove.

14. The metering device of claim 11 further having a detent in said mounting plate circumferentially spaced from said drop tubes in said circle to provide a fluid off position when said discharge opening is selectively aligned with said detent.

15. The metering device of claim 14 having a plurality of debosments extending from said disk toward said mounting plate, said debosments arranged generally the same as said drop tubes to retain said selection means in the selected position.

* * * * *

UNITED STATES PATENT AND TRADEMARK OFFICE
CERTIFICATE OF CORRECTION

PATENT NO. : 4,781,698

DATED : November 1, 1988

INVENTOR(S) : Mark L. Parren

It is certified that error appears in the above-identified patent and that said Letters Patent is hereby corrected as shown below:

On the title page, item [73]

insert -- Assignee: Parren-Donaldson, Inc.,
    St. Joseph, Michigan --.

Signed and Sealed this

Thirteenth Day of July, 1993

Attest:

MICHAEL K. KIRK

*Attesting Officer*      *Acting Commissioner of Patents and Trademarks*